United States Patent [19]
Puetter et al.

[11] Patent Number: 4,818,409
[45] Date of Patent: Apr. 4, 1989

[54] OBTAINING AQUEOUS SOLUTIONS OF ORGANIC ACIDS OR BASES FROM AQUEOUS SOLUTIONS OF THEIR SALTS

[75] Inventors: Hermann Puetter, Neustadt; Hartwig Voss, Ludwigshafen, both of Fed. Rep. of Germany

[73] Assignee: BASF Aktiengesellschaft, Ludwigshafen, Fed. Rep. of Germany

[21] Appl. No.: 842,466

[22] Filed: Mar. 21, 1986

[30] Foreign Application Priority Data

Apr. 20, 1985 [DE] Fed. Rep. of Germany ....... 3514348

[51] Int. Cl.$^4$ ............................................. B01D 13/00
[52] U.S. Cl. ..................................... 210/638; 210/644
[58] Field of Search .................... 210/644, 638, 321.2, 210/321.72

[56] References Cited

U.S. PATENT DOCUMENTS 4,306,946 12/1981 Kim .................................. 210/644 X
4,652,350 3/1987 Lipriano et al. ...................... 204/74
4,664,808 5/1987 Kim ..................................... 210/638

FOREIGN PATENT DOCUMENTS 126830 4/1984 European Pat. Off. ............ 210/638

Primary Examiner—Frank Spear
Attorney, Agent, or Firm—John H. Shurtleff

[57] ABSTRACT

Aqueous solutions of organic acids or bases are obtained by a process in which (a) an aqueous solution of a salt of an organic acid or of an organic base and (b) respectively, an aqueous solution of an inorganic base or of an inorganic acid are each passed into compartments of an exchange cell which are separated from one another by an ion exchange membrane, and the solution (a) and (b) are transported past the surface of the membrane.

16 Claims, No Drawings

OBTAINING AQUEOUS SOLUTIONS OF ORGANIC ACIDS OR BASES FROM AQUEOUS SOLUTIONS OF THEIR SALTS

The present invention relates to a process for obtaining aqueous solutions of organic acids or bases from aqueous solutions of their salts by ion exchange in an exchange cell.

Frequently acids or bases are obtained in the synthesis in the form of aqueous solutions of their salts. For example, the final stage of the Strecker synthesis for the preparation of amino acids involves alkaline or acidic hydrolysis of an aminonitrile, so that the amino acid is obtained either as a salt of an alkali metal or alkaline earth metal or a salt of a strong mineral acid. In order to obtain the amino acid in the free (betaine) form, these salts containing the groups $-COO^{\ominus}M^{\oplus}$ or $-NH_3^{\oplus}X^{\ominus}$ (where $M^{\oplus}$ is a metal cation and $X^{\ominus}$ is an acid anion) first have to be treated with an inorganic base or mineral acid.

Furthermore, in the synthesis of other organic acids which are readily water-soluble, such as hydroxycarboxylic acids, which are prepared, for example, by microbiological methods, and in the recovery of organic auxiliary bases, such as trimethylamine, aqueous salt solutions are obtained from which the free bases or acids are difficult to isolate. A further technical difficulty is that the free acids or bases have to be separated from the neutral salts, which are likewise readily soluble. This can be achieved by using ion exchangers or with the aid of electrolysis or electrodialysis.

However, these methods have disadvantages. For example, stoichiometric amounts of the particular resin in the $H^{\oplus}$ form or $OH^{\ominus}$ form are required in ion exchange processes. This large amount of ion exchange material required is uneconomical and also leads to product losses or greatly dilutes the desired product. In electrolysis, which is carried out, for example, in 3-compartment cells, not less than 1 Faraday of electricity has to be employed per neutralization equivalent. The consumption of electrical energy is considerable. In electrodialysis using bipolar membranes, electrode surface area and some of the energy required are saved compared with electrolysis; however, the consumption of electrical energy is nevertheless high since, in addition to overcoming the electrical resistance, energy is required for dissociation of the water.

We have found that aqueous solutions of organic acids or bases can be obtained from the aqueous solutions of their salts in a substantially more advantageous manner if (a) an aqueous solution of a salt of an organic acid or of an organic base and (b) respectively an aqueous solution of an inorganic base or of an inorganic acid are each passed into compartments of an exchange cell which are separated from one another by an ion exchange membrane, and the solutions (a) and (b) are transported past the surface of the membrane.

The disadvantages described are overcome by the process according to the invention. Instead of stoichiometric amounts of ion exchange material, ion exchange membranes are used, so that both product loss and dilution of the desired products are avoided. Furthermore, electricity for electrolysis or electrodialysis is not required in the novel process.

The process according to the invention results in the liberation of organic acids or bases with the aid of ion exchange membranes, through which the troublesome inorganic ions $M^{\oplus}$ or $X^{\ominus}$ can be exchanged for $H^{\oplus}$ or $OH^{\ominus}$. In contrast to ion transport using liquid membranes, where $M^{\oplus}/H^{\oplus}$ exchange also takes place, no carrier compound is required in this case to permit transport.

It is true that, for example European Pat. No. 126,830 discloses that sparingly soluble salts of anionic dyes can be converted to more readily soluble salts by ion exchange via an ion exchange membrane. However, it was not to be expected that the process of the present invention would make it possible to obtain the free acids or bases from their salts in such an advantageous manner, especially since the rate of exchange in the novel process is substantially higher than that in the conventional ion exchange process.

Examples of suitable salts of organic acids which can be converted to the free acids by the novel process are water-insoluble alkali metal, alkaline earth metal, copper, iron, zinc or chromium salts of organic acids. Examples of suitable organic acids are carboxylic acids, hydroxycarboxylic acids, amino acids, phosphonic acids or organic compounds which give an acidic reaction in an aqueous medium, eg. phenols, amides, sulfonamides or sulfonylamides. Preferred salts of acids are those having a water solubility of not less than 5, preferably not less than 10, % by weight. The organic acids may be monobasic or polybasic, and their $pK_a$ is preferably >2. For example, dicarboxylic acids or polycarboxylic acids are suitable. Of particular industrial interest is the recovery, according to the invention, of water-soluble hydroxycarboxylic acids, such as lactic acid, citric acid or sugar acids, or of amino acids, such as glycine, α- or β-alanin, N-alkylated derivatives of glycine or of alanin, aminobutyric acids, carnitine or anthranilic acids. Acids having molecular weights of <200 are preferred.

Examples of suitable salts of organic bases are water-insoluble salts of mineral acids, such as hydrochloric acid, sulfuric acid or phosphoric acid, on the one hand and monoacidic or polyacidic organic bases, such as amines, basic amino acids, heterocyclic compounds or quaternary ammonium compounds, on the other hand. Of particular industrial interest is the recovery, according to the invention, of water-soluble organic bases, such as trialkylamines, where alkyl is of 1 to 4 carbon atoms, or of auxiliary bases, such as diazabicyclooctane or dicyclohexylethylamine, or of polymeric amines, such as polyethylimines or polyvinylamines. Examples of preferred bases are amino acids, such as the above-mentioned ones, and quaternary ammonium compounds.

In the novel process, salts of polybasic acids may also be converted stepwise to the free acids. For example a tribasic salt, as trisodium citrate, can be converted with high selectivity to the disodium hydrogen compound or the monosodium dihydrogen compound. This also applies to the salts of polyacidic bases, which can be converted selectively and stepwise in a similar manner to the particular free bases. The salts of organic acids or bases are employed in the aqueous solutions in concentrations of, for example, from 1 to 40% by weight. The bases have a $pK_B$ of, preferably, >2.

Since the liberation of organic acids from their salts is based on the exchange of similarly charged ions between two aqueous solutions through the ion exchange membrane, an auxiliary solution (b) which contains an acid, such as an inorganic acid or a sulfonic acid, is required in addition to the process solution (a) which contains the salt of the organic acid. In the case of the liberation of a base, the process solution (a) contains the salt of the base, and the auxiliary solution (b) contains an inorganic base.

Examples of inorganic acids are mineral acids, such as hydrochloric acid or sulfuric acid. Examples of inorganic bases are inorganic compounds which contain $OH^{\ominus}$ groups or liberate these groups in water, eg. the hydroxides or carbonates of the alkali metals and alkaline earth metals and of ammonium. Preferred compounds here are NaOH, KOH, $Na_2CO_3$, $K_2CO_3$, Ca(OH)$_2$, Ba(OH)$_2$, $NH_4OH$ and $(NH_4)_2CO_3$. The stated acids and bases are used in the aqueous auxiliary solution in a concentration of, for example, from 0.1 to 10 equivalents per liter. Advantageously, not less than the stoichiometric amount, based on the organic acid or base to be liberated, of the acid or base is used, the amount employed expediently being from 1 to 10, preferably from 1 to 3, times the stoichiometric amount.

The process is carried out in an exchange cell which contains two or more compartments separated by an ion exchange membrane, so that two liquid streams separated from one another are possible. Exchange cells of this type are used, for example, for the conventional process of electrodialysis, except that the electrode compartments are dispensed with in the present case since an electric field is not required. A suitable apparatus is described in, for example, European Pat. No. 126,830. Examples of suitable exchange cells are apparatuses which are equipped with membrane stacks and contain a large number, eg. from 2 to 800, parallel compartments. However, since it is not necessary to apply an electric field, the procedure is not restricted to these flat-plate membrane modules. All other exchange cells, such as hollow fiber modules, tubular modules or spiral modules, may also be used. The compartments of the exchange cells, which are filled alternately with the aqueous solutions (a) and (b), are connected to, for example, external stock vessels in order to provide a flow past the membranes. The process may be carried out continuously or batchwise. In the batchwise process the solutions flow through the exchange cell repeatedly, while in the continuous process they flow through the exchange cell once. The two solutions can be passed through the exchange cell in parallel, in cross-flow or countercurrent to one another. Further exchange cells can be arranged in the form of a multi-stage cascade, particularly in the continuous procedure.

Suitable ion exchange membranes are conventional permselective cation exchange membranes or anion exchange membranes which are, for example, from 0.1 to 1 mm thick and have a pore diameter of from 1 to 30 $\mu$m or a gel-like structure. Membranes of this type are available commercially, for example, under the names ®Selemion, ®Neosepta and ®Nafion. Since a diffusion process is involved, particularly thin membranes, for example those having a thickness of >0.2 mm, are preferred. Cation exchange membranes are used for liberating the organic acids, while anion exchange membranes are required in ion exchange for the liberation of bases.

The process is carried out at from −20° to +80° C., preferably from +10° to +50° C., and under from 1 to 10 bar, preferably under atmospheric pressure. The pressure drop across the membranes used is from 0 to 5, in particular from 0 to 0.2, bar.

The novel process makes it possible to liberate water-soluble acids and bases from their salts in an economically advantageous manner, the resulting aqueous solutions of the acids or bases being free of undesirable inorganic substances.

Moreover, the process of the invention has unexpectedly high exchange rates.

EXAMPLE 1

Recovery of Citric Acid from the Trisodium Salt

The exchange cell used was a two-cycle membrane stack as conventionally used for electrodialyses, but without any electrode compartments in this case. The mineral acid used was hydrochloric acid. The trisodium citrate solution and the aqueous hydrochloric acid were circulated through alternate parallel compartments of the membrane stack, each via an external stock vessel. The membrane stack contained only cation exchange membranes, through which sodium ions were exchanged for hydrogen ions. The progress of the batchwise conversion was monitored by means of conductivity and pH measurements.

Details of the procedure are summarized below:
Method: batchwise operation (exchange of $Na^{\oplus}$ $H^{\oplus}$)
Membranes: cation exchange membranes available commercially under the name ®Selemion CMV and having a surface area of 0.15 m$^2$
Temperature: 25° C.
Process cycle:
  Feed: 20 l of a 0.05 molar aqueous trisodium citrate solution
  Discharge: 20 l of an aqueous solution having a hydrogen ion concentration of 0.148 mole/l and a citric acid concentration of 0.0507 mole/l (conversion 97%)
Auxiliary cycle:
  Feed: 35 l of 0.2 molar hydrochloric acid (1.3-fold stoichiometric excess)
Exchange rate [mol per m$^2$ per day]: mean=6, maximum=126.

EXAMPLE 2

Example 1 was repeated, except that, in order to obtain the monobasic, dibasic and tribasic acid, the experiment was terminated when the appropriate conversion (33 or 66 or 100%) was reached.

The mean exchange rate [mol per m$^2$ per day] was as follows for the three stages:

| 1 | 2 | 3 |
|---|---|---|
| Disodium citrate | Monosodium citrate | Citric acid |
| 123 | 117 | 47 |

EXAMPLE 3

Obtaining bistetrabutylammonium sulfate (BTBAS) from tetrabutylammonium hydrogen sulfate (TBAHS) using the two-cycle membrane stack described in Example 1.

Details of the procedure:
Method: batchwise operation (exchange of $HSO_3^{\ominus}$ for $OH^{\ominus}$)
Membranes: anion exchange membrane commercially available under the name ®Selemion DMV and having a surface area of 0.037 m$^2$ Temperature: 20° to 25° C.
Process cycle:
  Feed: a solution of 173.5 g (0.51 mole) of TBAHS in 2000 g of water
  Discharge: 2004 g (without samples) of an aqueous solution which contained 0.51 mole of BTBAS (conversion 100%)
Auxiliary cycle:
  Feed: 2 kg of a 1N sodium hydroxide Solution of (2.9-fold Stoichiometric excess)
Exchange rate [mol per m² per day]:
  Mean: 110
  Maximum: 250

EXAMPLE 4

Obtaining the monosodium salt of iminodiacetic acid (IDSHNa) from the disodium salt of iminodiacetic acid (IDSNa₂) using the two-cycle membrane stack described in Example 1.
Details of the procedure:
Method: batchwise operation (exchange of Na⊕ for H⊕)
Membranes: cation exchange membrane as described in Example 1, having a surface area of 0.02 m².
Temperature: 20° to 25° C.
Process cycle:
  Feed: 1800 g of an aqueous solution of 2.41 moles of IDSNa₂ which contain 0.2 mole of NaOH.
  Discharge: 1650 g (without samples) of an aqueous solution which contained 2.35 moles of IDSHNa.
Auxiliary cycle: 2 kg of 20% strength sulfuric acid (2.4-fold stoichiometric excess)
Mean exchange rate [mol per m² per day]: 80.

EXAMPLE 5

Obtaining γ-aminobutyric acid from the hydrochloride, using the two-cycle membrane stack described in Example 1.
Details of the procedure:
Method: batchwise operation (exchange of Cl⊖ for OH⊖)
Membrane: Anion exhcange membrane as described in Example 3, having a surface area of 0.037 m²
Temperature: 30° C.
Process cycle:
  Feed: A solution of 69.8 g (0.5 mole) of γ-aminobutyric acid hydrochloride in 2031 g of water.
  Discharge: 1860 g (without samples) of an aqueous solution which contained 0.5 mole of γ-aminobutyric acid and had a Cl⊕ content of 0.01%.
Auxiliary cycle: 2 kg of 1N NaOH (3-fold stoichiometric excess).
Exchange rate [mol per m² per day]:
  Mean=108
  Maximum=170.

We claim:

1. A process for obtaining an aqueous solution of a water-soluble organic acid which consists essentially of:
passing through alternate compartments of an exchange cell which is not exposed to an electric current, said cell having two or more compartments separated from one another by a cation exchange membrane,
(a) an aqueous solution of a salt of said organic acid, said acid having a pK$_a$ value >2, and
(b) an aqueous solution of a mineral acid, the respective solutions (a) and (b) being transported past opposite sides of the separating membrane.

2. A process as claimed in claim 1 wherein said salt of said organic acid has a water-solubility of not less than 5% by weight.

3. A process as claimed in claim 1 wherein said salt of said organic acid is an alkali metal or alkaline earth metal salt of an amino acid or a hydroxy carboxylic acid.

4. A process as claimed in claim 3 wherein said organic acid is citric acid.

5. A process as claimed in claim 3 wherein said organic acid is iminodiacetic acid.

6. A process as claimed in claim 1 wherein said inorganic acid is hydrochloric acid or sulfuric acid.

7. A process as claimed in claim 1 carried out at a temperature of from −20° C. to +80° C. and under a pressure of from 1 to 10 bar.

8. A process as claimed in claim 1 wherein said organic acid is selected from the group consisting of lactic acid, citric acid, sugar acids and amino acids having a molecular weight of 200.

9. A process as claimed in claim 1 wherein the amount of said mineral acid used is from 1 to 10 times the stoichiometric amount of the organic acid to be obtained.

10. A process as claimed in claim 1 wherein the amount of said mineral acid used is from 1 to 3 times the stoichiometric amount of the organic acid to be obtained.

11. A process for obtaining an aqueous solution of a water-soluble organic base which consists essentially of:
passing through alternate compartments of an exchange cell which is not exposed to an electric current, said cell having two or more compartments separated form one another by an anion exchange membrane,
(a) an aqueous solution of a salt of said organic base, said base having a pK$_B$ value >2, and
(b) an aqueous solution of an inorganic base, the respective solutions (a) and (b) being transported past opposite sides of the separating membrane.

12. A process as claimed in claim 11 wherein said salt of said organic base has a water-solubility of not less than 5% by weight.

13. A process as claimed in claim 11 carried out at a temperature of from −20° C. to +80° C. and under a pressure of from 1 to 10 bar.

14. A process as claimed in claim 11 wherein said salt of said organic base is an acidic salt of a quaternary ammonium compound and a polybasic mineral acid.

15. A process as claimed in claim 11 wherein the amount of said inorganic base used is from 1 to 10 times the stoichiometric amount of the organic base to be obtained.

16. A process as claimed in claim 11 wherein the amount of said inorganic base used is from 1 to 3 times the stoichiometric amount of the organic base to be obtained.

* * * * *